United States Patent [19]

del Valle

[11] Patent Number: 4,465,843
[45] Date of Patent: Aug. 14, 1984

[54] PROCESS FOR THE PREPARATION OF DERIVATIVES OF 2-PYRROLE ACETIC ACID WITH ANTI-INFLAMMATORY ACTIVITY

[75] Inventor: Margarita E. del Valle, Buenos Aires, Argentina

[73] Assignee: Laboratories Pharmedical SA, Luxembourg

[21] Appl. No.: 441,234

[22] Filed: Nov. 12, 1982

[30] Foreign Application Priority Data

Nov. 16, 1981 [ES] Spain .................................. 507.179

[51] Int. Cl.$^3$ ........................................ C07D 207/323
[52] U.S. Cl. ........................................................ 548/539
[58] Field of Search ............................................. 548/539

[56] References Cited

U.S. PATENT DOCUMENTS

3,752,826  8/1973  Carson .......................... 548/539 X
4,048,191  9/1977  Carson .............................. 548/539

Primary Examiner—Joseph Paul Brust
Attorney, Agent, or Firm—McAulay, Fields, Fisher, Goldstein & Nissen

[57] ABSTRACT

The derivatives of 2-pyrrole-acetic acid having the formula:

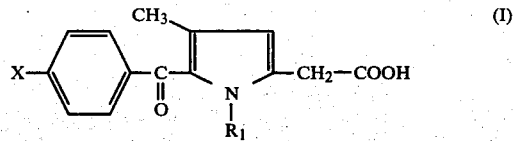

in which $R_1$ is methyl or ethyl and X is hydrogen or chlorine, have a powerful anti-inflammatory action.

These derivatives are prepared from ethyl 3,5-diethoxycarbonyl-4-methyl-2-pyrrole-acetate by alkylation, saponification, esterification, decarboxylation, benzoylation and saponification.

7 Claims, No Drawings

PROCESS FOR THE PREPARATION OF DERIVATIVES OF 2-PYRROLE ACETIC ACID WITH ANTI-INFLAMMATORY ACTIVITY

The present invention relates to novel anti-inflammatory agents, derived from 2-pyrrole-acetic acid and having the formula (I):

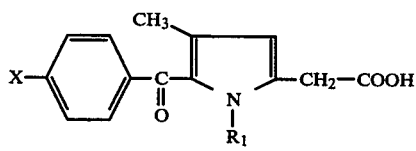

wherein
$R_1$ is $CH_3$ or $C_2H_5$ and
X is H or Cl

These compounds are endowed with a powerful activity, which is comparable with that of Indomethacin and, consequently, are better than phenylbutazone. The present invention in particular relates to a process for their preparation comprising a series of steps which are hereinafter in detail described.

1st Step

This step comprises forming the pyrrole ring (IV) by means of the Knorr reaction starting from ethyl beta-ketoglutarate (II) (as prepared according to the method described in Organic Synthesis 1, pages 10 and 237) and ethyl acetoacetate:

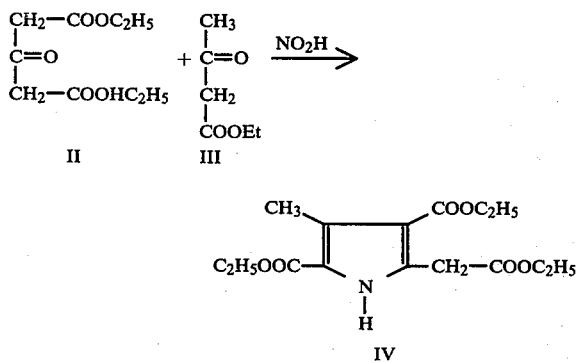

2nd Step

This step consists in the alkylation of compound (IV) by means of an alkylating agent, such as alkyl iodide or alkyl sulphate in an alkaline medium in the presence of a phase transfer agent to form compound (V):

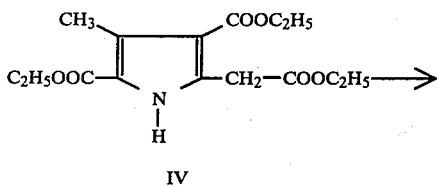

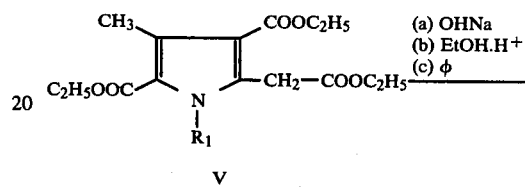

3rd Step

This step comprises the saponification, esterification and decarboxylation of compound (V) to give compound (VI):

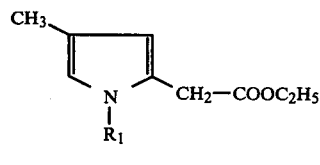

4th Step

This is the benzylation reaction in which compound (VI) is reacted with substituted benzoyl chloride, in the presence of tin chloride or aluminium chloride to give compound of formula (VII):

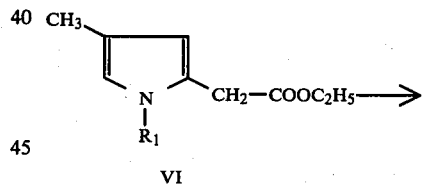

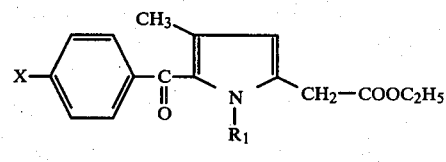

5th Step

The compound (VII) is saponified to form the compounds of formula (I):

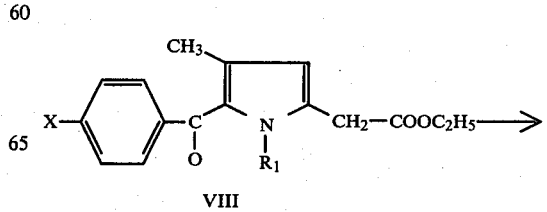

-continued

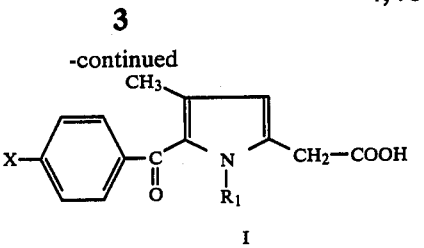

I

Pharmacological activity

A comparative study of the analgesic activity of representative compounds of the invention was carried out according to the method of the contorsions as induced by acetic acid by intraperitoneal route in the rat (Koster et al, Fed. Proc. 1959, 18, 442).

The following results were obtained:

TABLE 1

| Compound | $ED_{50}$ mg/kg p.os |
|---|---|
| acetyl salicylic acid | 110 |
| Example 1 | 22.0 |
| Example 2 | 2.5 |
| Example 3 | 31.0 |
| Example 4 | 82.0 |

A comparative study of the anti-inflammatory activity was carried out according to the method of the paw edema as induced by carrageenin in the female rat (Winter et al, Proc. Soc. Exp. Biol. (NY) 1962, 111, 544).

The following results were obtained:

TABLE 2

| Compound | $ED_{50}$ mg/kg p.os |
|---|---|
| Indomethacin | 2.85 (1.30–6.27) |
| Example 1 | 15.30 |
| Example 2 | 1.70 |
| Example 3 | 21.20 |
| Example 4 | 48.00 |

The following examples illustrate but do not limit the present invention.

(a) Synthesis of compound (IV): ethyl 3,5-diethoxycarbonyl-4-methyl-2-pyrrole-acetate In a suitable flask, fitted with an ampoule, thermometer, a stirrer and a refrigerating bath, there are charged 200 g of ethyl acetoacetate and 500 mls of acetic acid. The mixture is cooled to 5° C. and a solution of 120 g of sodium nitrite in 150 mls of water is added. The mixture is maintained at a temperature of between 30° and 40° C. for 3 hours. Then, 475 g of ethyl beta-ketoglutarate in ten portions and 220 g of zinc are added, taking care that the temperature does not become higher than 80°–85° C. The mixture is stirred for 4 hours and thereafter 10 liters of water are added. The raw product precipitates, is filtered and washed with water. It is crystallized again from ethanol, giving place to the pure compound (IV), having a melting point of 142°–144° C. Yield: 85%.

(b) Synthesis of compound (V): ethyl N-methyl-3,5-diethoxycarbonyl-4-methyl-2-pyrroleacetate. ($R_1=CH_3$)

312 g of the preceeding compound (IV), 3000 mls of acetone, 400 g of potassium carbonate and 10 g of benzyl-tributyl-ammonium bromide are charged in a flask and stirred.

There are then added dropwise with stirring 128 g of methyl sulphate, and the reaction is continued for 5 hours.

After filtration the solvent is evaporated under reduced pressure. The thus obtained residue is crystallized from isopropanol. Melting point: 155°–157° C. Yield: 65%.

If ethyl iodide (157 g) is used instead of methyl sulphate, ethyl N-ethyl-3,5-diethoxycarbonyl-4-methyl-2-pyrrole acetate is obtained.

Melting point: 142°–145° C. ($R_1=C_2H_5$).

(c) Synthesis of the compound (VI): ethyl N-methyl-4-methyl-2-pyrrolidin-acetate. ($R_1=CH_3$)

750 g of the above compound (V) are heated to reflux with 5000 mls of a 20% solution of sodium hydroxide pH is adjusted with hydrogen chloride before cooling and, after stirring of the reaction mixture at 5° C. for 2 hours, the product is crystallized and filtered. The raw product is esterified by treatment with 5000 mls of ethanol and 90 mls of concentrated sulfuric acid by refluxing for 1 hour. The mixture is cooled and filtered. The product is heated under nitrogen atmosphere for 3 hours at 190° C. until the gas development ceases. The resulting residue is distilled at 130° C. and 1 atm. In a manner like the above described one the N-ethyl derivative is prepared with the distillation being carried out at 140° C. and 1 atm.

(d) Synthesis of the compound (VII): ethyl N-methyl-4-methyl-5-benzoyl-2-pyrrolidineacetate ($R_1=CH_3$; $X=H$)

In a stirred flask having a refluxing refrigerant protected from moisture, 181 g of the preceeding compound (VI) are charged together with 1200 mls of 1,2-dichloroethane, 140 g of benzoyl chloride and 70 g of aluminium chloride. The mixture is maintained under stirring for 8 hours, and then poured into 2000 mls of water, cooled, made acidic with diluted hydrogen chloride and dried by means of magnesium sulphate. The residue product is concentrated and crystallized from isopropanol.

Melting point: 100°–102° C. Yield=63%.

By proceeding as above, the following compounds are prepared:

-ethyl-N-methyl-4-methyl-5-(4-chlorobenzyl)pyrrolidinacetate, $R_1=CH_3$; $X=Cl$; melting point: 95°–98° C.

-ethyl N-ethyl-4-methyl-5-benzoyl-2-pyrrolidine acetate;

$R_1=CH_2CH_3$; $X=H$; melting point: 99°–101° C.

-ethyl N-ethyl-4-methyl-5-benzoyl-2-pyrrolidine acetate.

$R_1=CH_2CH_3$; $X=H$; melting point: 93°–96° C.

EXAMPLE 1

Synthesis of compound (I)

N-methyl-4-methyl-5-benzoyl-2-pyrrolidine acetic acid. ($R_1=CH_3$; $X=H$)

285 g of the above compound (VII) are refluxed for 2 hours with 500 mls of a 2 N solution of sodium hydroxide. The reaction mixture is cooled and made acidic with hydrogen chloride then filtered and dried. The product is crystallized again from methanol/water.

Melting point: 165°–167° C. Yield: 80%

EXAMPLE 2

N-methyl-4-methyl-5-p-chloro-benzoyl-pyrrolidine acetic acid

In the benzoylation reaction for the synthesis of the compound (VII) ($R_1=CH_3$, $X=Cl$), p-chlorobenzoyl chloride is substituted for the benzoyl chloride, whereby the desired product is obtained, all the other steps being the same.

Melting point: 110°–112° C. Yield: 70%.

EXAMPLE 3

N-ethyl-4-methyl-5-p-chlorobenzoyl-2-pyrrolidin-acetic acid is obtained by proceeding as above and has a melting point of 105°–108° C. Yield: 55%.

EXAMPLE 4

N-ethyl-4-methyl-5-benzoyl-2-pyrrolidin-acetic acid is obtained by proceeding as above and has a melting point of 140°–143° C. Although the present invention was hereinbefore described with reference to specific embodiments, the same is not limited thereto and various modifications can be made therein without departing from its scope.

I claim:

1. A process for the preparation of derivatives of 2-pyrrole-acetic acid having the formula:

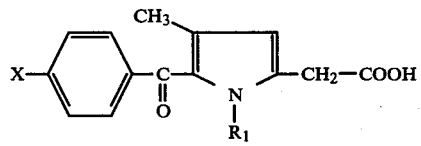

wherein $R_1$ is selected from the group of methyl and ethyl and X is selected from the group of hydrogen and chlorine, comprising the following steps:

(a) alkylation of ethyl 3,5-diethoxycarbonyl-4-methyl-2-pyrrole-acetate (IV) having the formula:

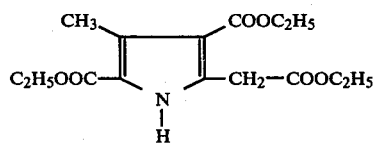

by means of an alkylating agent selected from the group of alkyl halides and alkyl sulphates wherein said alkyl is methyl or ethyl in an alkaline medium in the presence of a quaternary ammonium salt phase transfer agent to obtain N-alkyl-3,5-diethoxycarbonyl-4-methyl-2-pyrrole-acetate, having the formula:

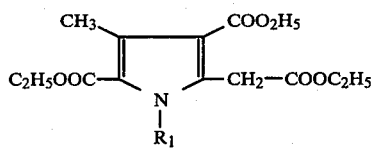

wherein $R_1$ is as above stated;

(b) saponification, esterification and decarboxylation of the derivative (V), in only one step, by means of an alkali agent and with ethanol and surfuric acid to form ethyl N-alkyl-4-methyl-2-pyrrolidine-acetate, having the formula:

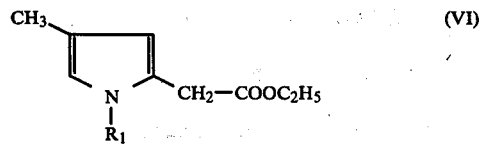

wherein $R_1$ is as above stated;

(c) benzoylating said compound (VI) with benzoyl chloride or p-chlorobenzoyl chloride in the presence of tin chloride or aluminum chloride, to obtain ethyl N-alkyl-4-methyl-5-benzoyl-2-pyrrolidine acetate, having the formula:

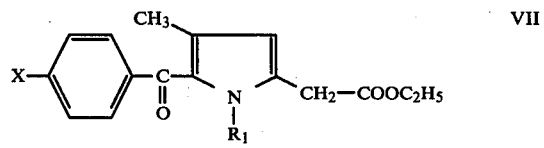

wherein $R_1$ is as above stated, and (d) saponifying compound (VII) with an alkali agent to form the compound of formula (I).

2. A process according to claim 1, wherein the alkylation of the compound (IV) is carried out by means of alkyl iodide or sulphate.

3. A process according to claim 2, wherein compound (IV) is prepared by reacting ethyl beta-ketoglutarate and ethyl acetoacetate in the presence of sodium nitrite and zinc at a temperature not higher than 85° C.

4. A process for the preparation of derivatives of 2-pyrrole-acetic acid having the formula:

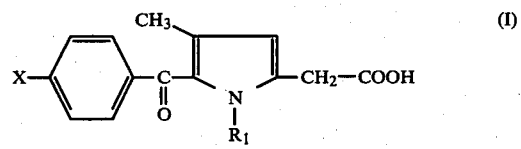

wherein $R_1$ is selected from the group of $CH_3$ and $C_2H_5$ and X is selected from the group of H and Cl, comprising the steps of:

(a) alkylating ethyl 3,5-diethoxycarbonyl-4-methyl-2-pyrroleacetate (IV) having the formula:

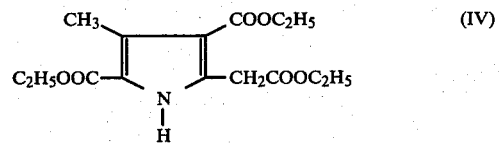

with an alkylating agent selected from the group of alkyl halides and alkyl sulphates wherein said alklyl is methyl or ethyl in an alkaline medium in the presence of a quaternary ammonium salt phase transfer agent to obtain N-alkyl-3,5-diethoxycarbonyl-4-methyl-2-pyrrole-acetate, having the formula:

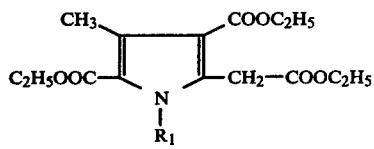

wherein $R_1$ is as above stated;

(b) saponifying said compound (V) with an alkaline agent, esterifying with a mixture of ethanol and a mineral acid selected from the group of sulphuric acid and hydrogen chloride, at refluxing temperature for at least one hour and decarboxylating under an inert atmosphere at a temperature of at least 190° C. to form ethyl N-alkyl-4-methyl-2-pyrrolidine-acetate, having the formula:

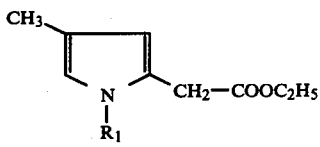

wherein $R_1$ is as above stated;

(c) benzoylating compound (VI) with a compound selected from the group of benzoyl chloride and p-chloro benzoyl chloride in the presence of tin chloride or aluminum chloride, to obtain ethyl N-alkyl-4-methyl-5-benzoyl-2-pyrrolidine acetate having the formula:

![Formula VII: a pyrrole ring with CH3 at position 4, CH2-COOC2H5 at position 2, N-R1, and a para-X-phenyl-C(=O)- group at position 5] (VII)

wherein $R_1$ is as above stated; and (d) saponifying compound (VII) with an alkali metal hydroxide at reflux temperature to form the compound of formula (I).

5. A process according to claim 4, wherein alkylation of compound (IV) is carried out by means of alkyl iodide or alkyl sulphate.

6. A process according to claim 4, wherein compound (IV) is prepared by reacting ethyl beta-ketoglutarate and ethyl acetoacetate in the presence of sodium nitrite and zinc at a temperature not higher than 85° C.

7. A process according to claim 4, wherein said quaternary ammonium salt is benzyl tributylammonium bromide.

* * * * *